US012161492B2

(12) United States Patent
Beucher et al.

(10) Patent No.: US 12,161,492 B2
(45) Date of Patent: Dec. 10, 2024

(54) RADIOLOGICAL IMAGING METHOD

(71) Applicant: EOS IMAGING, Paris (FR)

(72) Inventors: Jérôme Beucher, Esbly (FR); Pascal Desaute, Paris (FR); Khrystyna Kyrgyzov, Sceaux (FR); Audrey Lemoussu, Issy les Moulineaux (FR); Pierre Morichau-Beauchant, Paris (FR); Hamid Ouamara, Arcueil (FR)

(73) Assignee: EOS IMAGING, Paris (FR)

( * ) Notice: Subject to any disclaimer, the term of this patent is extended or adjusted under 35 U.S.C. 154(b) by 275 days.

(21) Appl. No.: 17/776,022

(22) PCT Filed: Jul. 15, 2020

(86) PCT No.: PCT/EP2020/070058
§ 371 (c)(1),
(2) Date: May 11, 2022

(87) PCT Pub. No.: WO2021/094004
PCT Pub. Date: May 20, 2021

(65) Prior Publication Data
US 2022/0386972 A1 Dec. 8, 2022

(30) Foreign Application Priority Data
Nov. 14, 2019 (WO) .................. PCT/IB2019/001291

(51) Int. Cl.
*A61B 6/50* (2024.01)
*A61B 6/00* (2006.01)
(Continued)

(52) U.S. Cl.
CPC .......... *A61B 6/4014* (2013.01); *A61B 6/4241* (2013.01); *A61B 6/505* (2013.01); *A61B 6/544* (2013.01)

(58) Field of Classification Search
CPC ..... A61B 6/4014; A61B 6/4241; A61B 6/505; A61B 6/544; A61B 6/405; A61B 6/4266;
(Continued)

(56) References Cited

U.S. PATENT DOCUMENTS

2004/0086076 A1 5/2004 Nagaoka et al.
2004/0101179 A1 5/2004 Suryanarayanan et al.
(Continued)

FOREIGN PATENT DOCUMENTS

JP 2002102218 A 4/2002
JP 2002263097 A 9/2002
(Continued)

OTHER PUBLICATIONS

International Search Report mailed Oct. 13, 2020, in corresponding to International Application No. PCT/EP2020/070058; 3 pages.
(Continued)

*Primary Examiner* — David P Porta
*Assistant Examiner* — Mamadou Faye
(74) *Attorney, Agent, or Firm* — Maier & Maier, PLLC

(57) ABSTRACT

A radiological imaging method including 2 radiation sources with imaging directions orthogonal to each other, performing vertical scanning of a standing patient along a vertical scanning direction, wherein radiological method includes at least one operating mode in which: a frontal scout view is made so as to identify a specific bone(s) localization within the frontal scout view, driving current intensity modulation of the frontal radiation source, depending on patient thickness and on the identified specific bone(s) localization along the vertical scanning direction, is performed automatically, so as to improve a compromise between: lowering the global radiation dose received by a patient during the vertical scanning, while keeping at a sufficient level the local image contrasts of the identified specific bone(s) localization at
(Continued)

different imaging positions along the vertical scanning direction, for the frontal image.

23 Claims, 14 Drawing Sheets

(51) Int. Cl.
 *A61B 6/40* (2024.01)
 *A61B 6/42* (2024.01)
(58) Field of Classification Search
 CPC ....... A61B 6/488; A61B 6/5258; A61B 6/542; A61B 6/545; A61B 6/4007; A61B 6/4258; G05B 13/027; G06N 3/02
 See application file for complete search history.

(56) References Cited

U.S. PATENT DOCUMENTS

| | | | |
|---|---|---|---|
| 2005/0008219 | A1 | 1/2005 | Pomero et al. |
| 2011/0026668 | A1 | 2/2011 | Wu et al. |
| 2016/0242712 | A1 | 8/2016 | Jin et al. |
| 2017/0119331 | A1* | 5/2017 | Brody ................ G16H 50/20 |
| 2019/0046133 | A1* | 2/2019 | Beucher ............. A61B 6/4007 |
| 2019/0083047 | A1 | 3/2019 | Miller et al. |
| 2019/0246999 | A1 | 8/2019 | Liu et al. |
| 2019/0290234 | A1 | 9/2019 | Kuwabara |

FOREIGN PATENT DOCUMENTS

| | | |
|---|---|---|
| JP | 2006527434 A | 11/2006 |
| JP | 2015205063 A | 11/2015 |
| JP | 2019166155 A | 10/2019 |
| WO | 2019008407 A1 | 1/2019 |

OTHER PUBLICATIONS

Written Opinion of the International Searching Authority mailed Oct. 13, 2020, in corresponding to International Application No. PCT/EP2020/070058; 5 pages.
Office Action issued on Feb. 27, 2023, in corresponding Japanese Application No. 2022-528120, 13 pages.
Office Action issued on Apr. 1, 2024, in corresponding Japanese Application No. 2022-528116, 9 pages.
Written Opinion issued on Jul. 17, 2020, in corresponding International Application No. PCT/IB2019/001291, 7 pages.
Office Action issued on Oct. 18, 2022, in corresponding British Application No. GB2208712.6, 6 pages.
Office Action issued on Apr. 19, 2024, in corresponding British Application No. GB2206990.0, 3 pages.
Office Action issued on Oct. 4, 2023, in corresponding British Application No. GB2206990.0, 4 pages.
Office Action issued on Jan. 22, 2024, in corresponding British Application No. GB2206990.0, 3 pages.

* cited by examiner

RADIOLOGICAL IMAGING METHOD

FIELD

The invention relates to radiological imaging methods, wishing to lower radiation dose received by patient, whereas still wanting to obtain patient body images of good quality.

BACKGROUND

A scanning stereo-radiographic system demonstrated interesting capabilities to make simultaneous frontal and lateral images for 3D reconstruction of skeletal anatomical parts such as the rachis or pelvis with a dose reduction up to 50 or even up to 100 compared to CT (Computed Tomography) Scan. and also a dose reduction up to 10 for single view images compared to classical CR (Computed Radiography) or DR (Direct Radiography) systems.

But this system did not have an AEC (Automatic Exposure Control), and thus the parameters of the patient scan were only manually chosen by the operator according to the evaluation he can do visually on the patient anatomy. He could only choose between three possible anatomy sizes, small, medium or large. The spectrum characteristics (kV and filter) and intensity of the X-ray beam were tuned referring to a simple table according to the choice of the protocol (full body, full spine, pelvis . . . ) and the size of the patient (small, medium or large). This system was interesting to help operator to choose the parameters, but the main drawback was linked to the only visual choice of the operator.

This drawback was also known for standard 2D radiology, and some Automatic Exposure Control (AEC) was developed to enable automatic exposure duration. This kind of AEC could stop the exposure as soon as the dose target is reached in a dosimeter cell, which is usually a radiolucent ionisation chamber, placed between the patient and the detector (film, CR, DR). This kind of AEC had also some drawbacks. A first drawback is linked again on the choice of the operator for the spectrum (kV, filter) usually selected with a crossed choice on the protocol and the size of the patient typically among 3 possibilities. A second drawback of this kind of AEC was linked to the kind of detector used to acquire the image. As long as films were used, this kind of AEC could provide correct results, because over exposure or under exposure effects are clearly visible on films which provides too light or too dark images density. Thus, the dose target of the AEC could be set to get a standard expected density for a kind of film. But when the Computed Radiography (CR) and Direct Radiography (DR) captors began to be widespread 2D detectors for radiology, other problems appeared because the operator could not anymore simply detect an over exposure or under exposure looking at the light or black image density, because these detectors and their automatic image processing can provide almost the same kind of image density whatever the dose, the only difference is the noise in the image. The operators had some difficulties to set properly the dose target according to noise in images, and the use of different kind or suppliers of CR or DR detectors models was also a cause of notable difficulties to get good results.

IEC 62494-1 proposed to use an Exposure Index (EI) which relies on the noise and thus on the Signal to Noise Ratio (SNR) of the image to define the dose target of the AEC as an Exposure Index Target (EIT). IEC 62494-1 also proposed to define a Deviation Index (DI) as the ratio of reached Exposure Index to the Exposure Index Target expressed in decibel $DI=10*\log_{10}(EI/EIT)$.

Considering a scanning radiography system, the known methods of AEC for standard 2D radiography using a dosimeter cell placed between the patient and the detector are hardly compatible for different reasons. A first reason is linked to the great difficulty or even the impossibility to change the exposure time which is linked only on the scan speed and the size of the scanned area, where for the 2D systems the AEC dosimeter cell doesn't move with respect to the patient, and therefore this static measure for 2D systems enables to stop the exposure as soon as the exposure target is reached. A second reason is the field of view of such a dosimeter for a scanning radiography system which would rely only on the very tiny part of the relevant ROI (Region of Interest) for the diagnosis in the patient body, typically only one line of the total image. The use of such a tiny part of the relevant ROI has little chance to provide a-priori information which would be required to process the parameters of the shot to get an Exposure Index in a relevant ROI close to the Exposure Index Target and to get a satisfactory Signal to Noise Ratio (SNR).

According to a first prior art outside of the technical field of radiological vertical scanning imaging, it is known a computed tomography imaging method based on a rotating radiation source emitting a very high radiation dose, in patent application US 2011/0026668, performing an helical path along an horizontal scanning direction of a patient lying on a patient bed. This radiation source is driven by both a current intensity and by a voltage intensity. Current intensity is linked to the quantity of radiation dose emitted by a radiation source in a unit of time, for example in a second. Voltage intensity is linked to the energy of each emitted photon by the radiation source. For performing such horizontal scanning of a given specific lying patient, voltage intensity is modulated so as to adapt emitted radiation dose along the horizontal scanning direction or current intensity is modulated along the horizontal scanning direction so as to adapt emitted radiation dose, which is anyway very high, and at least fifty times higher than in vertical scanning of a standing patient, to the patient thickness along the horizontal direction and so as to improve the global image contrast to the patient thickness along the horizontal direction.

SUMMARY

The object of the present invention is to improve the compromise between:
  lowering radiation dose received by patient,
  and maintaining a good level of image quality of patient body or of patient organ, or at least keeping at a sufficient level the image quality of patient body or of patient organ,
  while using a radiological imaging method:
    which is globally easier and simpler as the one of the first prior art previously mentioned.
    and especially which can use a much simpler and cheaper current modulation radiation generator, since this current modulation radiation generator will have to modulate current intensity without being constrained by any additional voltage intensity modulation.

The invention proposes to solve the problem, in vertical scanning of a standing patient, where anyway the emitted radiation dose is much lower than in computed tomography, of still reducing this emitted radiation dose, while simultaneously looking for maintaining a good or at least sufficient level of image contrast differently along said vertical direction depending on patient thickness variation along said vertical scanning direction, by modulating quantity of emitted radiation particles without changing the energy of the beam.

Thereby emitted radiation dose is reduced at low thickness zones of patient body and kept minimized while being maintained at a still sufficient emitted radiation dose at high thickness zones of patient body, while using a rather simple and cheap current intensity modulation radiation generator to modulate current intensity, thereby leading to improving globally emitted radiation dose.

Such compromise between reduced emitted radiation dose and sufficient image contrast, while making simple and cheap the used radiological imaging method, is possibly different at each height along said vertical scanning direction, or least changing often with variable thickness of patient body along said vertical scanning direction.

Moreover, this local image contrast is maintained at a sufficient level or better maintained at same level (as in first prior art):
not globally only depending on the global thickness of the patient,
but also locally in patient body regions where patient thickness is the highest which are indeed most critical patient body regions for imaging, guided on the specific bone(s) localization identified in the scout view(s),
while using a simpler and cheaper radiological imaging method, especially when using a simpler and cheaper current intensity modulation radiation generator to modulate current intensity without any voltage intensity modulation during imaging.

Keeping at a sufficient level the local image contrasts of said identified specific bone(s) localization at different imaging positions along said vertical scanning direction means that the level of the local image contrasts are, not lowered or deteriorated, or at least not too much lowered or deteriorated so that they would imply no more correctly seeing said identified specific bone(s) for the practitioner of the radiological imaging method.

In other words, keeping at a sufficient level the local image contrasts of said identified specific bone(s) localization at different imaging positions along said vertical scanning direction means that the level of the local image contrasts are sufficient for the practitioner of the radiological imaging method to see and notice possible lesions within said identified specific bone(s) localization.

Keeping at a sufficient level the local image contrasts of said identified specific bone(s) localization at different imaging positions along said vertical scanning direction means ideally maintaining the local image contrasts of said identified specific bone(s) localization at different imaging positions along said vertical scanning direction.

Keeping at a sufficient level these local image contrasts means preferably maintaining the local image contrast at least for the patient regions or patient zones which are the thickest.

Knowing which patient regions or patient zones are the thickest can be done via the scout view(s).

This object is achieved with a radiological imaging method comprising: 2 radiation sources with imaging directions orthogonal to each other, one frontal radiation source and one lateral radiation source, sliding vertically so as to perform vertical scanning of a standing patient along a vertical scanning direction, wherein said radiological method comprises at least one operating mode in which: a frontal scout view is made by performing a preliminary vertical scanning of a standing patient along said vertical scanning direction by said frontal radiation source, said frontal scout view is processed to identify a specific bone(s) localization within said frontal scout view, a driving current intensity of at least said frontal radiation source is modulated along said vertical scanning direction, depending on patient thickness and on said identified specific bone(s) localization along said vertical scanning direction, with no modulation of voltage intensity of said frontal radiation source along said vertical scanning direction, said driving current intensity modulation of said frontal radiation source is performed automatically, so as to improve a compromise between: lowering the global radiation dose received by a patient during said vertical scanning, while keeping at a sufficient level the local image contrasts of said identified specific bone(s) localization at different imaging positions along said vertical scanning direction, for the frontal image. Voltage is synonym of tension.

This object is also achieved with a radiological imaging method comprising: 2 radiation sources with imaging directions orthogonal to each other, one frontal radiation source and one lateral radiation source, sliding vertically so as to perform vertical scanning of a standing patient along a vertical scanning direction, wherein said radiological method comprises at least one operating mode in which: a lateral scout view is made by performing a preliminary vertical scanning of a standing patient along said vertical scanning direction by said lateral radiation source, said lateral scout view is processed to identify a specific bone(s) localization within said lateral scout view, a driving current intensity of at least said lateral radiation source is modulated along said vertical scanning direction, depending on patient thickness and on said identified specific bone(s) localization along said vertical scanning direction, with no modulation of voltage intensity of said lateral radiation source along said vertical scanning direction, said driving current intensity modulation of said lateral radiation source is performed automatically, so as to improve a compromise between: lowering the global radiation dose received by a patient during said vertical scanning, while keeping at a sufficient level the local image contrasts of said identified specific bone(s) localization at different imaging positions along said vertical scanning direction, for the lateral image.

This object is also achieved with a radiological imaging method comprising: 2 radiation sources with imaging directions orthogonal to each other, one frontal radiation source and one lateral radiation source, sliding vertically so as to perform vertical scanning of a standing patient along a vertical scanning direction, wherein said radiological method comprises at least one operating mode in which: frontal and lateral scout views are made by performing a preliminary vertical scanning of a standing patient along said vertical scanning direction by said frontal and lateral radiation sources, said frontal and lateral scout views are processed to identify a specific bone(s) localization within both said frontal and lateral scout views, driving current intensities of both said frontal and lateral radiation sources are modulated along said vertical scanning direction, depending on patient thickness and on said identified specific bone(s) localization along said vertical scanning direction, with no modulation of voltage intensities of either frontal or lateral radiation sources along said vertical scanning direction, said driving current intensity modulation of said frontal radiation source, as well as said driving current intensity modulation of said lateral radiation source, are all performed simultaneously, preferably synchronously, and automatically, so as to improve a compromise between:

lowering the global radiation dose received by a patient during said vertical scanning, while keeping at a sufficient level the local image contrasts of said identified specific bone(s) localization at different imaging positions along said vertical scanning direction, for the frontal image and for the lateral image.

Preferred embodiments comprise one or more of the following features, which can be taken separately or together, either in partial combination or in full combination, with any preceding object of the invention.

Preferably, said identified specific bone(s) localization includes a patient spine, preferably is a patient spine.

Indeed, patient spine is the specific bone(s) localization which is the most interesting to analyze in detail within a patient body; therefore it is used to drive and current intensity modulation.

Alternatively, the specific bone(s) localization may also be a pelvis or an arm or a leg of a standing patient along a vertical scanning direction, depending on the region of interest within the part of patient body which is imaged.

Preferably, said driving current intensity modulation of said frontal radiation source is performed also so as to reach a value of signal to noise ratio which is constant and common to most of said imaging positions along said vertical scanning direction, preferably to all said imaging positions along said vertical scanning direction, for said frontal image and/or for said lateral image, but which can take two different values respectively for frontal image and for lateral image.

Preferably, for each of said frontal and/or lateral images, said signal to noise ratio value is constant and predetermined for each different patient organ to be imaged.

Preferably, for a frontal image of a patient spine, said standard signal to noise ratio value corresponds to a number of X-ray photons received per detector pixel comprised between 50 and 70, the radiological imaging method operator preferably having the possibility to deviate, via a manual command, from this standard value by at least + or −20%, more preferably by at least + or −50%, and/or for a lateral image of a patient spine, said standard signal to noise ratio value corresponds to a number of X-ray photons received per detector pixel comprised between 20 and 40, the radiological imaging method operator preferably having the possibility to deviate, via a manual command, from this standard value by at least + or −20%, more preferably by at least + or −50%.

Hence, with a constant and optimized signal to noise ratio along, or even all along, said vertical scanning direction, the local image contrasts of the identified specific bone(s) localization at different imaging positions along said vertical scanning direction are much improved, for what was indeed the region of interest within the frontal and/or lateral images.

Preferably, said frontal and/or lateral image, after having undergone at least a first step of current intensity modulation, is normalized preferably by homogenization of regions located just outside patient body contours, in order to get rid of image artifacts coming from said driving current intensity modulation.

Indeed, because of this driving current intensity modulation, there were some artifacts in the frontal and/or lateral images, which were superposing some alternating waves of clear and dark grey levels on blank parts of the image just outside the patient) or in very thin parts of the patient, rendering those images a bit less comfortable to interpret for the radiological imaging method operator, or at least needing some training on his or her side.

Preferably, said frontal and/or lateral image, after having been normalized, undergoes a contrast enhancement step.

Hence, on the one side image artifacts coming from this driving current intensity modulation are cancelled whereas contrast enhancement improved by this same driving current intensity modulation are not only kept but also fully taken advantage of.

Preferably, said identified specific bone(s) localization excludes metallic parts, if any, as for example metallic prosthesis of part of skeleton of patient body or as for example metallic protections put in place on patient body before performing said radiological imaging method.

Indeed, these foreign (to patient body) objects introduced within or on patient body, since being metallic and therefore stopping much more radiation, and X-ray, than the rest of patient body, can lead to some non-optimization of the emitted dose, risking to lead, for the altitudes corresponding to these foreign objects, to some over exposure or to some under exposure to emitted radiation. In modes, first where driving voltage intensity is constant, and all the more second when both driving voltage intensity and driving current intensity are constant, if metal outliers are not excluded, consequences can be worse since more or all parameters are chosen for a maximal thickness, thereby emitted a radiation dose higher or much higher than needed, what would be very detrimental to patient.

Preferably, said current intensity modulation is maximized so as to also maximize said vertical scanning speed at a constant value.

Hence for a given emitted radiation dose, so for a given radiation dose received by standing patient during said vertical scanning, both kept at same level, the total vertical scanning time is notably reduced, having the advantage of lowering the possibility for the standing patient to move and the effects of a patient move, thereby reducing somewhat the risk of blurring and the risk of deformation of the frontal and lateral images, thereby still enhancing the signal to noise ratios of these frontal and lateral images.

Preferably, said operating mode can be either switched on or switched off manually by a radiological imaging method operator.

Hence, this very advantageous way of operating a radiological imaging apparatus is available whereas it can be cancelled if and when the operator of this radiological imaging apparatus wants to get rid of it, in order for instance to fully manually operate this radiological imaging apparatus. The radiological imaging method according to advantageous embodiments of the invention presents 3 operating modes: a full manual mode, an AEC mode without modulation, an AEC mode with modulation.

Preferably, said operating mode is dedicated to vertical scanning of large and/or obese patients.

Preferably, said operating mode is dedicated to vertical scanning of children patients.

The radiological imaging method according to the invention is all the more interesting that the thickness of the patient can be especially lower or especially higher than for an averaged size patient. This shows the capability of the radiological imaging method according to the invention to be very patient specific. Of course, the radiological imaging method according to the invention works also very well for standard sized patients.

Preferably, said current intensity modulation(s) rate do(es) not go beyond a predetermined threshold of 5 mA per millisecond, preferably a predetermined threshold of 2 mA per millisecond, more preferably a predetermined threshold of 1 mA per millisecond.

Hence, the radiological imaging method according to the invention can be performed also with relatively simple and cheap radiation sources with relatively slow current intensity driving capabilities.

Preferably, said current intensity modulation(s) at least range(s) from 20 mA to 300 mA, and preferably from 10 mA to 400 mA.

Hence, the radiological imaging method according to the invention can be performed also with relatively simple and cheap radiation sources with relatively limited ranges of current intensity driving capabilities. Preferably, said fixed voltage intensity is selected within a range from 50 kV to 120 kV.

Hence, the radiological imaging method according to the invention can be performed also with relatively simple and cheap radiation sources.

Preferably, said vertical scanning speed value at least range(s) from 8 cm/second to 20 cm/second, and preferably from 4 cm/second to 30 cm/second.

Hence, the radiological imaging method according to the invention can be performed also with relatively simple and cheap radiation sources with relatively limited extent of ranges of vertical scanning speed capabilities, while at the same time fully taking advantage of available ranges of vertical scanning speed capabilities.

Preferably, each of said frontal and/or lateral scout view(s) is made by performing a preliminary vertical scanning of a standing patient along a vertical scanning direction with a reduced global radiation dose as compared to each of said frontal and lateral images, before making each of said frontal and lateral images.

Hence, the modulation of driving current intensity, as well as possibly of vertical scanning speed, depending on the thickness profile and on the specific bone(s) localization of standing patient body along the vertical scanning direction, can be determined just before performing the vertical scanning which will result in effective frontal and lateral images of standing patient body performed with a limited but full radiation dose sufficient to make high quality frontal and lateral images. The scout view(s) can be performed at the cost of quite a limited over exposure to emitted radiation.

Preferably, said reduced global radiation is less than 10% of said global radiation dose, preferably less than 5% of said global radiation dose.

Hence, the benefit is double: not only is the over exposure during scout view performance (+10% or +5%) very limited, but also it is very efficient to optimize compromise between global radiation dose received and enhancement of image contrast.

Preferably, pixels in said scout view are gathered together, preferably by zones of N×N pixels, more preferably by zones of at least 10×10 pixels, to make imaged zones, for example by zones of at least 20×20 pixels to make imaged zones.

Hence, image quality and image contrast are enhanced for the scout view, despite the very low level of emitted radiation dose used to perform this scout view.

Preferably, said images or said imaged zones are processed to identify salient points which in turn are used to compute said thickness profile and to identify said specific bone(s) localization of a standing patient along said vertical scanning direction.

Hence, it is easier and more efficient to compute said thickness profile and to identify said specific bone(s) localization of a standing patient along the vertical scanning direction, from the scout view, despite the very low level of emitted radiation dose.

Preferably, said images or said imaged zones are processed by a neural network to compute said thickness profile and to identify said specific bone(s) localization of a standing patient along said vertical scanning direction.

Hence, it is easier and more efficient to identify said specific bone(s) localization of a standing patient along the vertical scanning direction, from the scout view, despite the very low level of emitted radiation dose.

Preferably, said 2 radiation sources slide vertically so as to perform vertical scanning of a pelvis or of a spine or of a full body of a standing patient along a vertical scanning direction.

Preferably, 2 radiation detectors are respectively associated with said 2 radiations sources, said 2 radiation detectors being 2 Photon Counting Detectors (PCD) each being associated to an automatic image processing function balancing automatically image density whatever radiation dose received on the sensitive surface of said radiation detector to enhance image contrast.

Hence, over exposure or under exposure to radiation signal emitted by radiation sources is harder to be correctly assessed manually by the radiological imaging method operator. Besides, Photon Counting Detectors present improved linearity and signal to noise ratio, as compared to gaseous detectors.

Preferably, 2 radiation detectors are respectively associated with said 2 radiations sources, said 2 radiation detectors being 2 multi-energy counting detectors, preferably being 2 Energy Resolved Photon Counting Detectors (ERPCD).

Preferably, radiation is X-ray.

A standing patient or a patient in a standing position is a patient who is in a weight bearing position, contrary to a lying patient or to a patient who is in a lying position as in computed tomography. Another patient weight bearing position, alternative to patient standing position could be a patient seating position.

Further features and advantages of the invention will appear from the following description of embodiments of the invention, given as non-limiting examples, with reference to the accompanying drawings listed hereunder.

DETAILED DESCRIPTION

Figure 1:
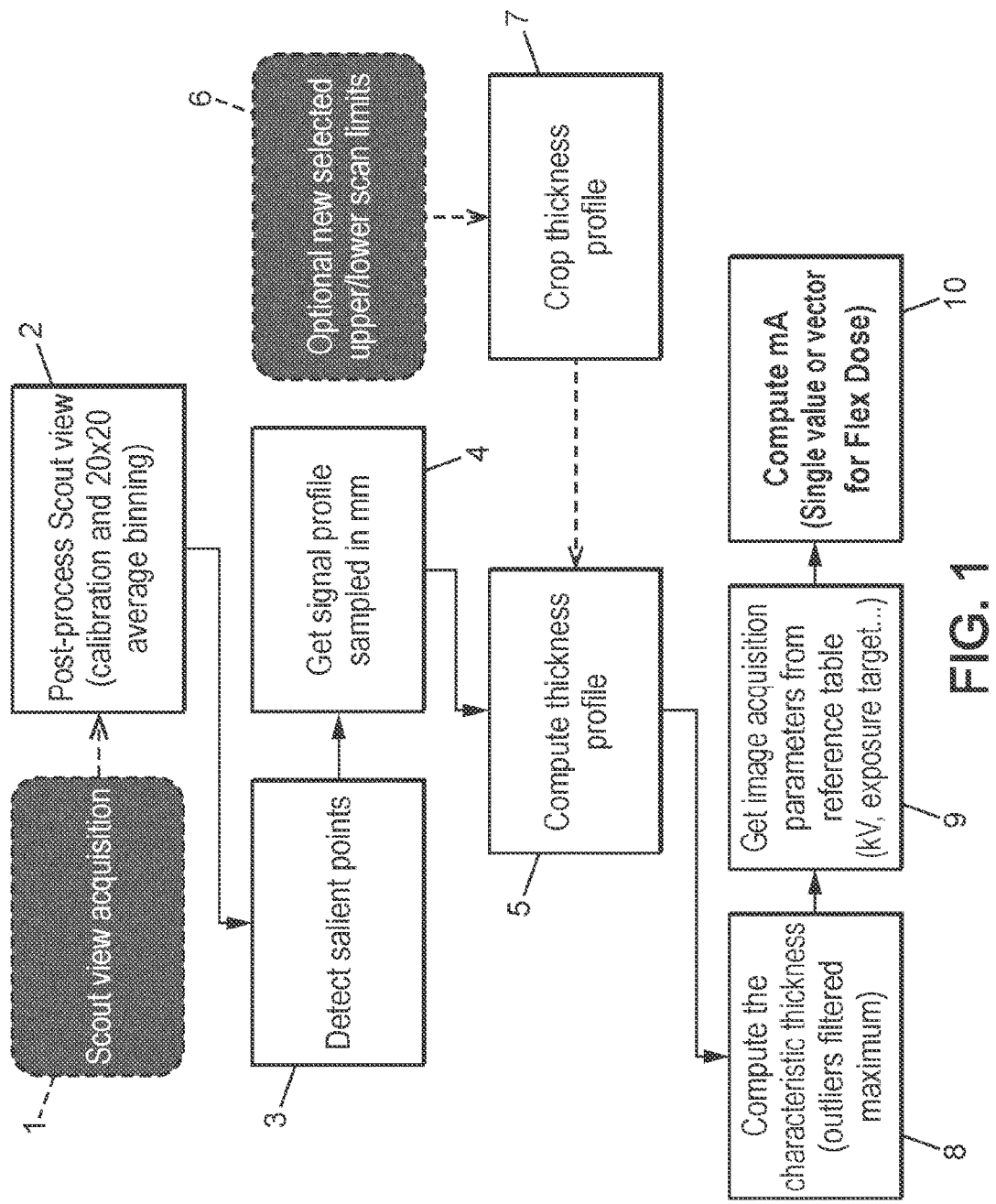
FIG. 1 shows an example of a part of the radiological imaging method according to an embodiment of the invention, dealing with computing driving current intensity modulation of radiation source.

The present invention aims at providing a solution to provide an AEC system to a scanning stereo-radiographic system, this AEC being compliant to the IEC 62494-1. This AEC system is designed to be used in the scanning stereo-radiographic system described in the applications PCT/IB2016/000273 and PCT/IB2017/000986, incorporated by reference and owned by same applicant EOS-Imaging.

In a preferred embodiment, the two detectors of this scanning stereo-radiographic system are multi-energy counting detectors, also known as Energy Resolved Photon Counting Detector (ERPCD) with at least 2 energy bins. In another embodiment, the two detectors of this scanning stereo-radiographic system are mono-energy counting detectors also known as Photon Counting Detector (PCD).

The use of the photon counting detector, in multi-energy or in mono-energy is advantageous compared to the gaseous detector for two main reasons. The first reason is the fact that the signal of the ERPCD or PCD is linear with the incoming flux and is directly equal to the number of detected photons while the signal of the gaseous detector was strongly non-linear, and this non-linearity was rather complex to model to correct it with precision. In the ERPCD and PCD a non-linear behavior still exists at high flux called the pile-up effect, but this pile-up effect can be well modeled and corrected by the image calibration software. The second reason is the fact that the ERPCD and PCD have a very stable behavior and sensitivity without the need of a new calibration during months and are not sensible to a room temperature variation, where the gaseous detector was far to be as stable and needed a daily calibration, and its behavior and sensitivity could also vary in a few minutes according to a change of room temperature. The stability of the PCD and ERPCD and the photon counting functionality enable to use directly the counting signal of incident photon in the detector to evaluate the Exposure Index and the Signal to Noise Ratio. The Signal to Noise Ratio is directly equal to the root mean square of the signal. Other kinds of energy integration detector, as the gaseous one for example, do not present this advantage and need to precise calibration to evaluate the SNR, and thus the Exposure Index.

The radiological imaging method according to embodiments of the invention is based on the use of a scout view, in mono-energy (ERPCD or PCD). As one goal of this scanning radiography system is dedicated to bones imaging for orthopedics, the scout view in that case is analyzed to find precisely the axial skeletal or bones of the selected protocol. But for some other applications, a soft tissue organ protocol as for instance the lung could be selected, and in that case the scout view is analyzed to find the organ.

The relevant ROI for the diagnosis according to the definition of IEC 62494-1 is defined by the union of a set of circular sub ROI also called 'patch' of approximately the size of a vertebrae (4-5 cm diameter), which are placed on the set of characteristics detected points or landmarks on the scout view according to a protocol specific search of bones or organs. This search of characteristics points can be embodied with two different methods: a specific salient point search algorithm or using a trained pose detection Deep Neural Network.

Then the equivalent thickness of the patient is evaluated in each patch, and some protocol of specific selection rules provides a vertical vector of equivalent thickness according to the Z (vertical) position in the patient. The equivalent thickness is evaluated in mono material PMMA [Poly (methyl methacrylate)] equivalent when mono-energy scout view is used.

The vertical equivalent thickness vector is then used to process a characteristic thickness, which is a secured detection of most probable maximum thickness. The characteristic thickness and the equivalent vector thickness are then used to process the parameters of the scan to get an Exposure Index in each patch as close as possible to the Exposure Target.

The exposure parameters can be produced in a few different modes according to the choice of the operator:
  a first mode called 'constant exposure mode' provides simply the optimal constants kV, mA, filter and scan speed to use for the scan and will provide a Constant flux exposure control according to the definition of the IEC 60601-2-44;
  a second mode called 'Flex Dose' will process a scan speed, a selected filter and a vector of temporal modulation of the exposure along the vertical axis and will provide a Z axis exposure control according to the definition of the IEC 60601-2-44.

The "Flex Dose" is to be used with the voltage or tension (kV) being fixed and the current (mA) being modulated along the Z axis. The operating mode according to the invention is this second mode called "Flex dose".

FIG. 1 shows an example of a part of the radiological imaging method according to an embodiment of the invention, dealing with computing driving current intensity modulation of radiation source.

The radiological imaging method according to embodiments of the invention includes a method to process the current intensity modulation of a radiation source along the vertical scanning direction. The FIG. 1 presents the functional block diagram of an example implementation using the salient points.

The following successive steps are performed:

In a step 1, a scout view of the standing patient is acquired with reduced radiation dose. The Scout View is required in order to use the "Flex Dose" mode and is acquired with a 0.5 mm thickness copper filter and a very low dose. The patient dose ratio between this Scout View and the main shot is less than 10% for long axis and localized protocols. This step 1 of the method is the acquisition of a scout view at reduced dose by a vertical scanning along the patient.

In a step 2, a post processing of the scout view is performed where pixels in the scout view are gathered together, preferably by zones of N×N pixels, for example by zones of at least 20×20 pixels, to make imaged zones with calibration and average binning. The Scout View was here acquired at such a low level of dose that a large binning 20×20 was applied to filter enough of the noise and get a higher level of confidence on the estimated thickness. This step 2 is the post processing of the scout view image, including the homogeneity correction using the gain calibration of the detector, and the use of a filter to improve the signal to noise ratio without introducing any bias to get a high level of confidence on the estimated thickness, for instance an average binning of 20×20 is well adapted.

Figure 9:
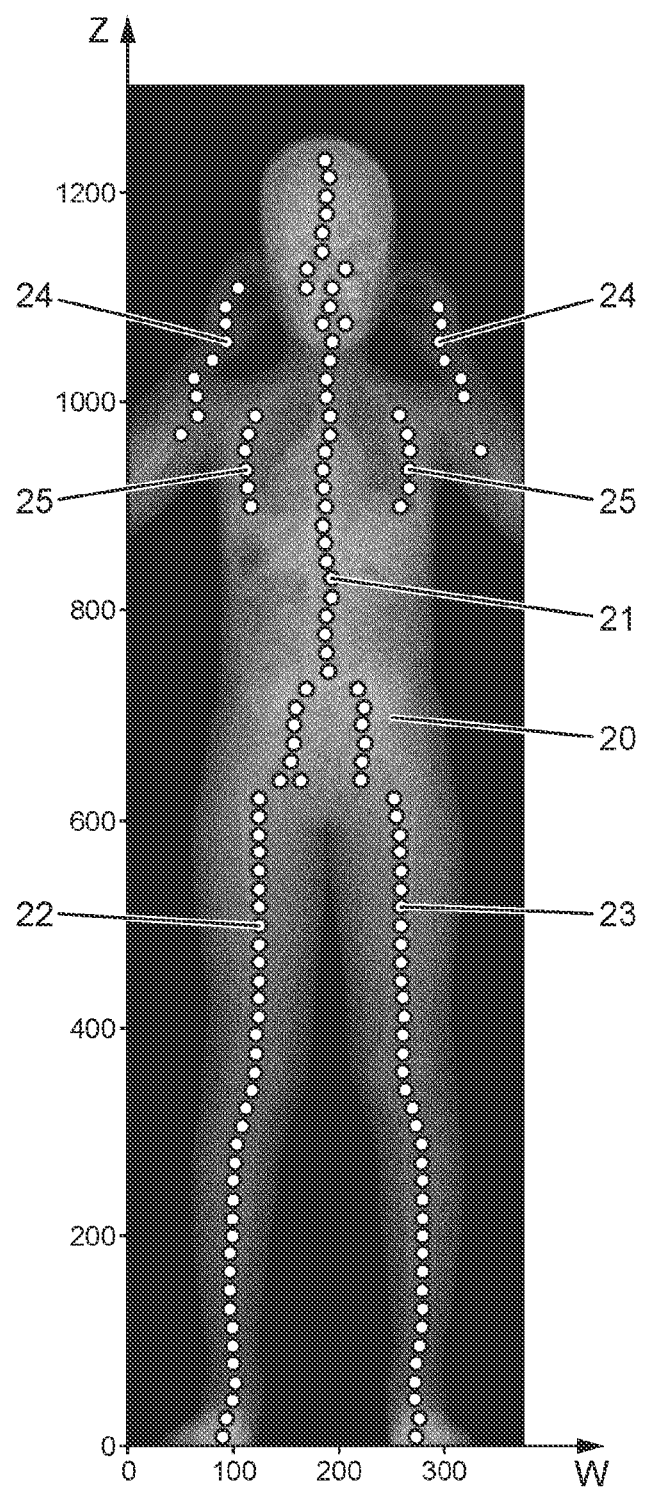
FIG. 9 shows an example of a filtered frontal scout view, after salient points detection step, but before salient points filtering step.
Figure 10:
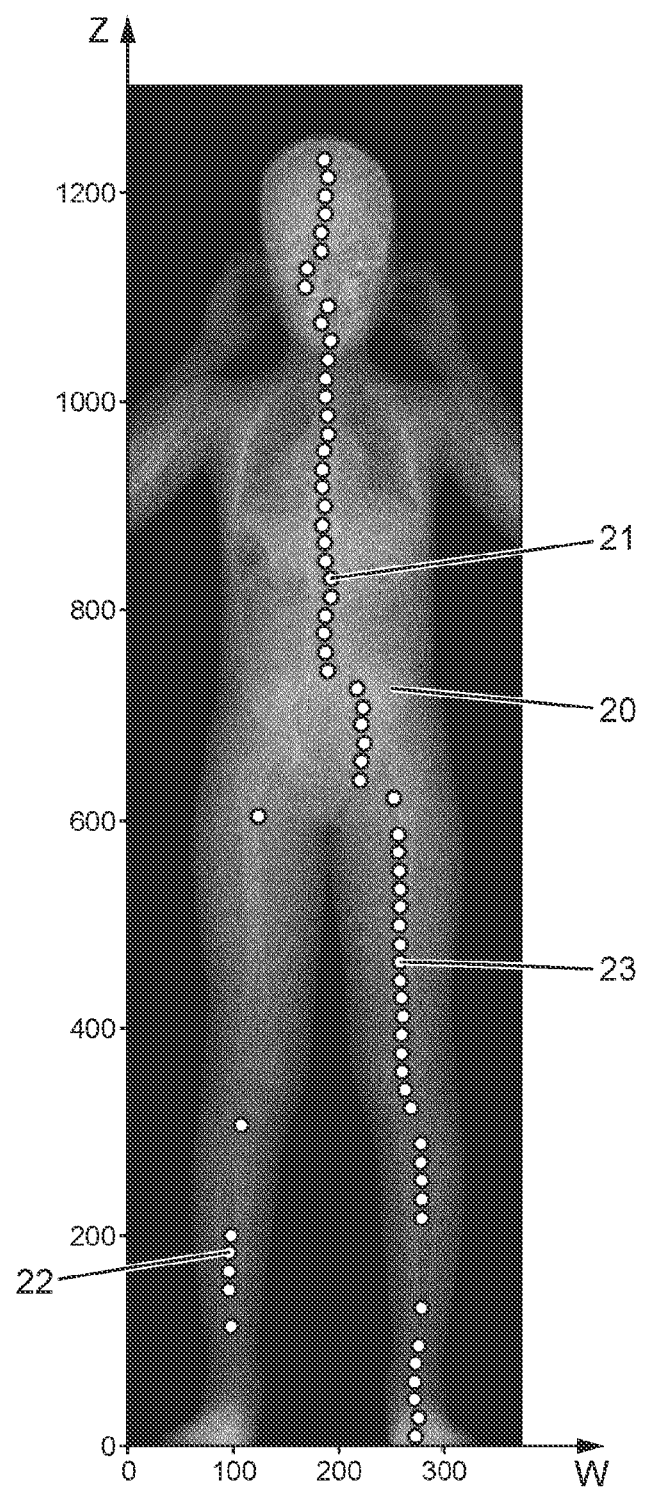
FIG. 10 shows an example of a filtered frontal scout view, after salient points detection step and after salient points filtering step.
Figure 11:
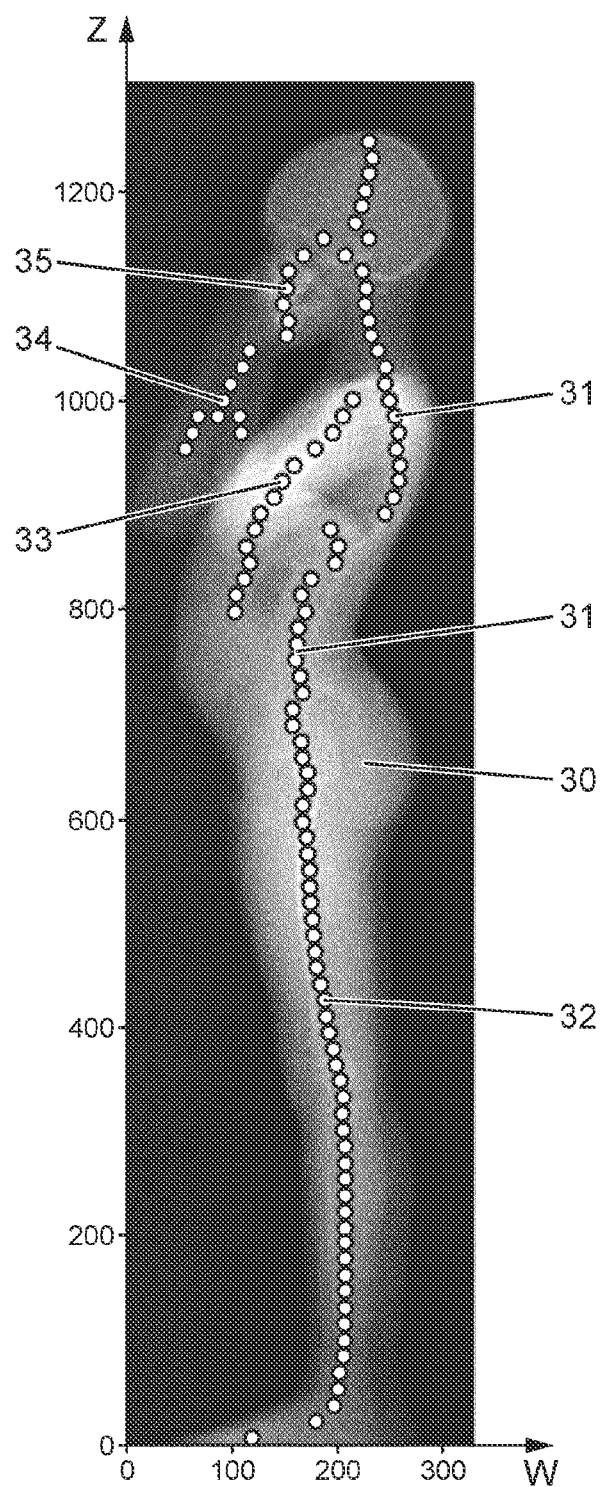
FIG. 11 shows an example of a filtered lateral scout view, after salient points detection step, but before salient points filtering step.
Figure 12:
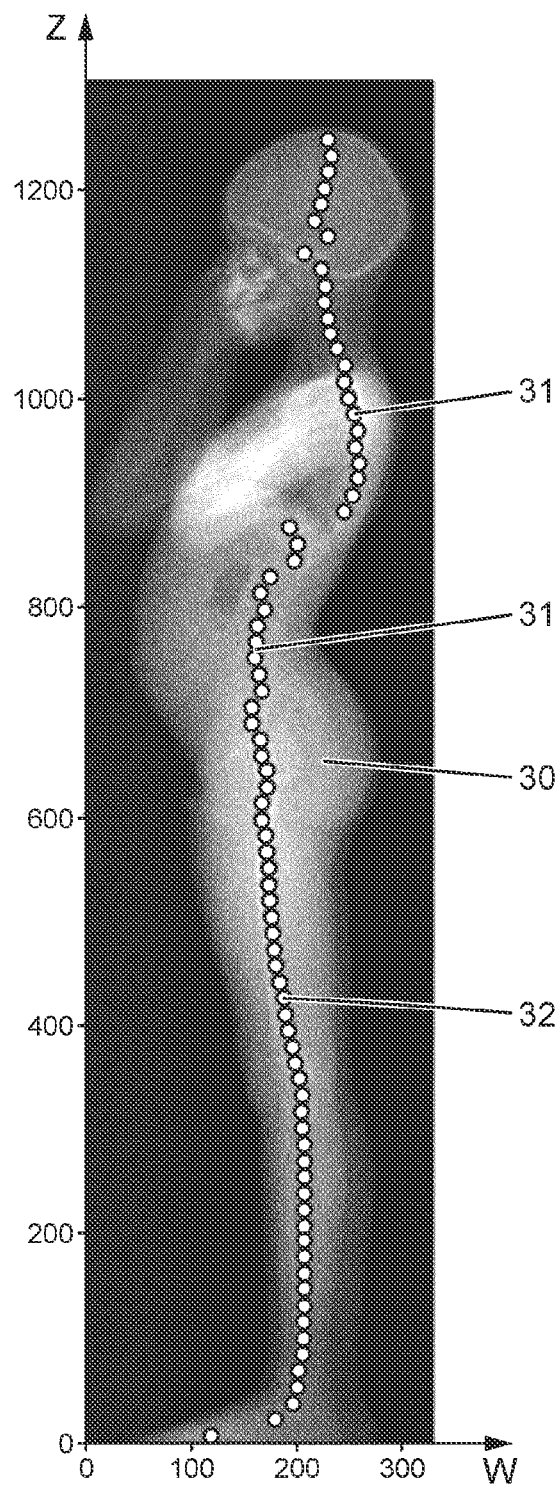
FIG. 12 shows an example of a filtered lateral scout view, after salient points detection step and after salient points filtering step.
Figure 13:
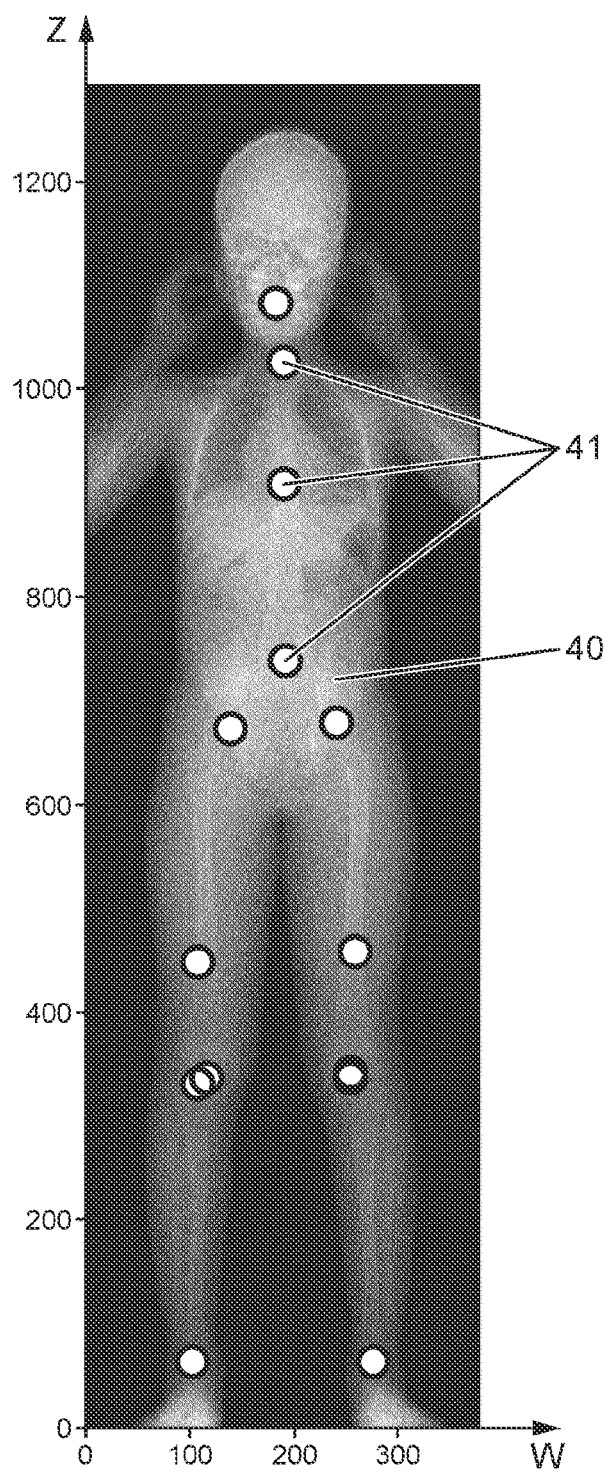
FIG. 13 shows an example of a filtered frontal scout view, after deep neural network detection step.
Figure 14:
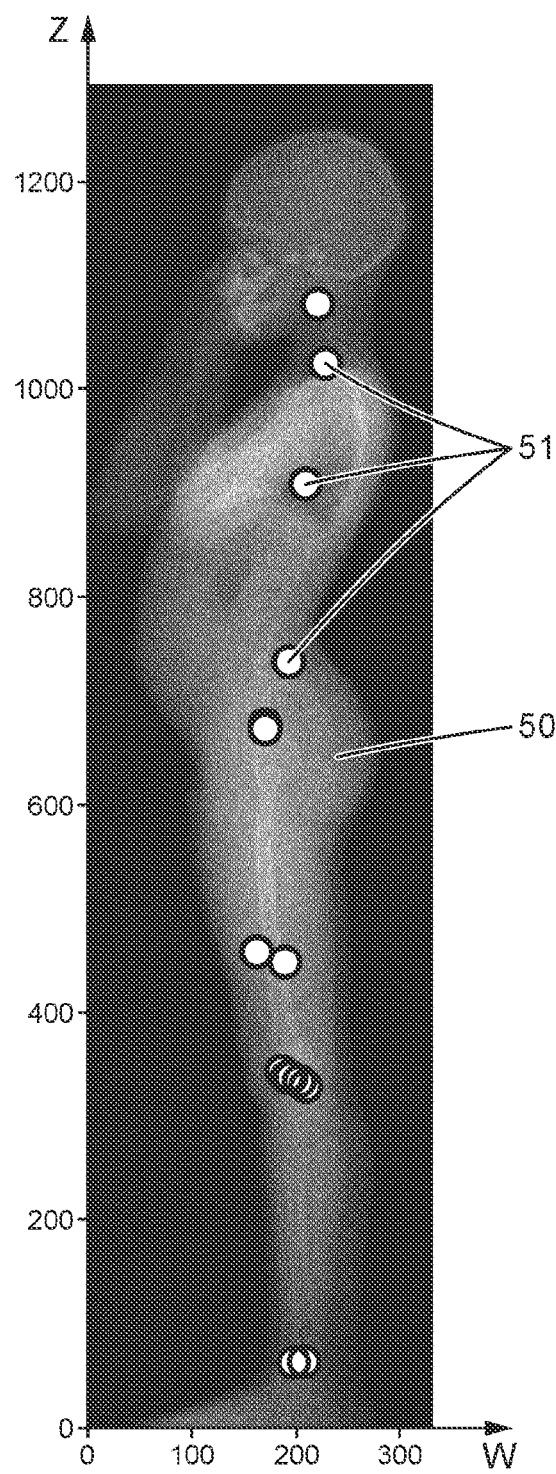
FIG. 14 shows an example of a filtered lateral scout view, after deep neural network detection step.

In a step 3, salient points are detected as will be explained in more detail with respect to FIGS. 9 to 12, where first points of higher radiation absorption are detected, and where then part of detected points are filtered out according to predetermined rules, in order to keep practically only the wished specific bones localization, for example the patient body spine, giving the salient points succession. A salient point detection algorithm developed to detect validated axial skeletal bones is applied on the binned image. The detected salient points are then selected differently in frontal and lateral images according to the patient orientation. The selected salient points mainly follow the axial skeletal composed of the lower limbs, the pelvis, the spine, the neck, and the head. A metal prosthesis or metal protection detection is also used to remove and to exclude the corresponding selected salient points in step 3 where metal detection is performed whereas in step 8 the outliers are just selected with respect to thickness. This step 3 is the detection of the specific bone(s) localization and rejection of metal parts in the scout view. As a matter of example, we use the description of the method using the salient points detection, but another implementation using a specific neural network can also be used. The salient points detection method used consists to search at a scale of a typical vertebrae size, which is around 5 cm diameter, to find a set of local maximum attenuation points in the scout view. The detected salient points are then selected differently in frontal and lateral images according to the patient orientation. The selected salient points mainly follow the axial skeletal composed of the lower limbs, the pelvis, the spine, the neck, and the head. There exists only one selected salient point at one Z altitude (at one Z position along vertical scanning direction) whereas there can be several different detected salient points at one Z altitude. The FIGS. 9 to 12 present respectively the salient points detection and selection on the frontal and lateral scout view of a patient. The FIGS. 9 and 11 present the detected salient points, and the FIGS. 10 and 12 present the selected salient points. The FIGS. 13 and 14 present an example of the skeletal detection using the neural network method, including a limited number of landmarks, applied on the same patient than for the FIGS. 9 to 12. As a matter of example, the limited number of landmarks presented in the FIGS. 13 and 14 correspond to the cervical vertebras C2 and C7, the thoracic vertebra T9, the sacrum, and on the lower limbs the left and right femoral head, ⅓ diaphysis, center of trochlea, distal tibia and proximal tibia. The selection of salient points method enables also to remove the points which are detected on metallic parts, including for example metallic prosthesis or metallic protections for breast, gonad ovary or other sensible parts of the body. The metallic parts can also be removed using the neural network method.

In a step 4, from the salient points, a signal profile is obtained as a function of vertical position expressed in mm. This step 4 is the processing of signal profile along the vertical scanning of the patient. The median value of the signal of the scout view image is processed in each circular patch centered on selected salient points and is associated to the altitude z of the corresponding salient point in the vertical scanning referential. The patch size representing an area approximately equivalent to a vertebrae size which is around 5 cm diameter. The resulting signal profile function of z is sparse, and an interpolation and extrapolation of this sparse signal profile provides a complete vertical profile sampling of signal according to the vertical altitude z on the whole height of the required vertical scanning of the patient, including some bottom and top extension of scan area for optional selection by the operator.

In a step 5, from preceding signal profile, a patient thickness profile is computed. Indeed, this step 5 is the processing of the thickness profile along the vertical scanning of the patient. The logarithm of the signal profile function of c is processed using a calibration second degree polynomial function to provide the corresponding PMMA thickness equivalent according to the equation 1:

$$t = \begin{cases} a\left[\ln\left(\frac{signal}{mAs}\right)\right]^2 + b\left[\ln\left(\frac{signal}{mAs}\right)\right] + c, \text{ if signal} > 0 \\ MaxThickness, \text{ if signal} = 0 \end{cases}$$

with mAs=mA$_{scout\ view}$*time_per_line and MaxThickness=600 mm of PMMA.

The coefficients a, b and c of the polynomial are processed using a calibration.

In a step 6, optionally, new upper and/or lower scan limits can be manually selected by radiological imaging method operator. The operator can reduce or increase a little bit the height of the scan using a selection tool on the scout view images in the interface software.

In a step 7, optionally, the patient thickness profile is cropped according to preceding new upper and/or lower scan limits. The processed thickness profile function of z is then cropped according to the operator selection of the upper and lower limits of the vertical scan along the patient.

In a step 8, from preceding thickness profile, a characteristic patient thickness is computed, after filtering out outliers like metallic prosthesis or metallic protections has already be done in step 3. This step 8 is the processing of the characteristic thickness. Considering simply the maximum value of the thickness profile previously determined at the step 5 is not representative of patient's thickness when patient is sitting or with a leg on a support or with folded arms. To define a representative thickness of the patient, the derivative of the thickness profile is processed to define statistical parameters using the mean and standard deviation to remove outliers, and then the characteristic thickness is defined as the maximum thickness without considering the outliers.

In a step 9, image acquisitions parameters are taken from a reference table, according both to specific bones localization, for instance precise position of the patient spine along vertical scanning direction, and to patient thickness variation along vertical scanning direction, i.e. along height of the patient. Indeed, the processed characteristic PMMA equivalent thickness and the selected protocol are used to obtain the image acquisition parameters (kV, filter, scan speed) according to a reference anatomical parameters table. The step 9 is the selection in a table of the image acquisitions parameters according to the processed characteristic thickness and to the selected protocol. The parameters set comprises for instance the signal target, and the reference kV. The reference kV, mA and speed could be used to acquire the images of the patients in case the operator choose to disable the modulation, but to keep the AEC, in that case, the scan speed and the constant value of current would be processed according to the signal target and to the characteristic thickness. The reference voltage (kV) is used to acquire the images of the patients with the current modulation with a constant voltage (kV). As a matter of example, the signal target for a spine exam are different for the frontal and the lateral images and are typically respectively around 60 photons/pixel for frontal view, and around 30 photons/pixel for lateral view. These values can be adjusted by the radiologist in a limited allowed range.

In a step 10, depending on the chosen operating mode, either a constant value of current intensity, or preferably a variable modulation of current intensity along the vertical direction is chosen, as a function of both the precise position of the patient spine along vertical scanning direction and the patient thickness variation along vertical scanning direction, in order to reach a constant and common signal to noise ratio along vertical scanning direction. i.e. a constant target number of X-ray photons per detector pixel along vertical scanning direction, this constant target number of X-ray photons per detector pixel along vertical scanning direction having preferably a different value for frontal image, for example 60, and for lateral image, for example 30. The final step of the "Flex Dose" mode is the processing of the current (mA) modulation vector of the image along the patient body part to scan to fit the Exposure Index Target as close as possible in every patch of the ROI. A matrix was calibrated to establish the relationship between the measured signal values as a function of a set of voltage (kV) values and PMMA equivalent thicknesses. The algorithm used to determine the current (mA) performs 1D interpolation within this matrix.

More precisely, in this step 10, depending on the chosen operating mode, a variable modulation of current intensity along the vertical direction are chosen, as a function of both the precise position of the patient spine along vertical scanning direction and the patient thickness variation along vertical scanning direction so as to get an equivalent patient thickness variation along vertical scanning direction (bones attenuate more radiation, therefore they equivalent to superior thicknesses than their real thicknesses, as compared to soft tissues), in order to reach a constant and common signal to noise ratio along vertical scanning direction, i.e. a constant target number of X-ray photons per detector pixel along vertical scanning direction, this constant target number of X-ray photons per detector pixel along vertical scanning direction having preferably a different value for frontal image, for example 60, and for lateral image, for example 30.

The contrast is known to be better at low voltage (kV) but, the use of a low voltage (kV) is not efficient looking at the useful dose which provides some signal in the detector compared to the dose received in the thick parts of a body. The choice of a specific value of the voltage (kV) constant along the complete vertical scanning, when one or more voltage values are available (at least 3, and preferably exactly 3, of them are available), is guided by a compromise between a better contrast leading to a lower voltage (V) and a more efficient dose use leading to a higher voltage (kV). The thickness profile, and a 1D table representing the expected signal with respect to the chosen constant voltage value and to the thickness for a referenced current and scan speed is used to process the required current profile at the reference scan speed to reach the signal target. The current profile can be then adjusted proportionally to a specific scan speed. For instance, it is required to double the current profile to double the scan speed with respect to the reference scan speed. The source having a maximum output power, the maximum current profile allowed for a given scan speed can be deduced by the ratio of the maximum power and the chosen constant voltage value. The optimal scan speed is found looking at the higher allowed current profile.

The final step of the "Flex Dose" mode is the processing of the of the current (mA) modulation vector of the image along the patient body part to scan to fit the Exposure Index Target as close as possible in every patch of the ROT.

The voltage (kV) and current (mA) can be processed only as scalar values for the corresponding characteristic thickness in constant AEC mode, or as a current modulation vector in "Flex Dose" mode to optimize the X-ray flux according to the estimated thickness of the patient along the vertical scan. The "Flex Dose" mode enables an important dose reduction for long axis protocols compared to a constant current (mA) mode, which was based only on the maximum thickness of the patient.

The overall target of "Flex Dose" mode is to reach a constant and repeatable signal level on the maximum thickness location of the patient's scanned area in constant mode, and moreover, to reach a constant and repeatable signal level all along the scanned axial skeletal of the patient and independently of the patient morphology and thickness for this mode.

Figure 2:
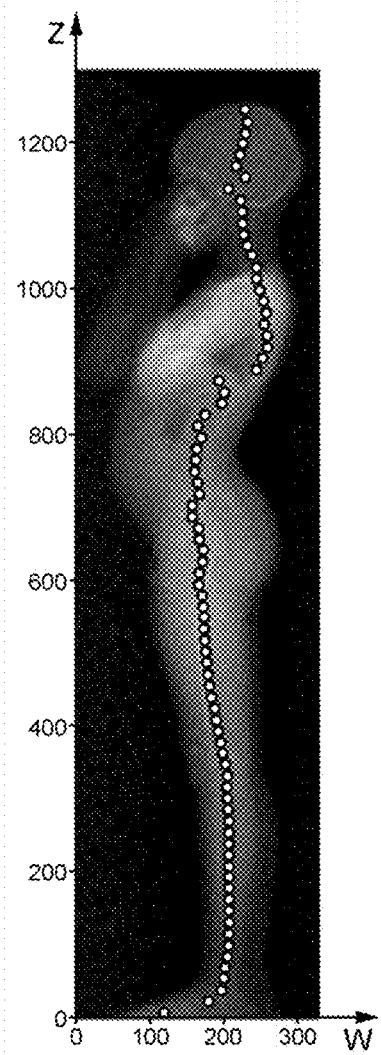
FIG. 2 shows an example of a specific bones localization, here a patient full body including a spine continued by pelvis and leg, via salient points detection.

FIG. 2 shows an example of a specific bones localization, here a patient full body including a spine continued by pelvis and leg, via salient points detection. The FIG. 2 presents a typical example of selected salient points on a lateral scout view.

The succession of circles follows the patient spine in a globally vertical direction. This succession of salient points SP is spotted on the lateral image of a patient body. This patient body lateral image is plotted with respect to altitude Z (height along vertical scanning direction) as a function of the patient width, patient thickness th being perpendicular to plan of figure, both altitude and width w being expressed in mm.

Figure 3:
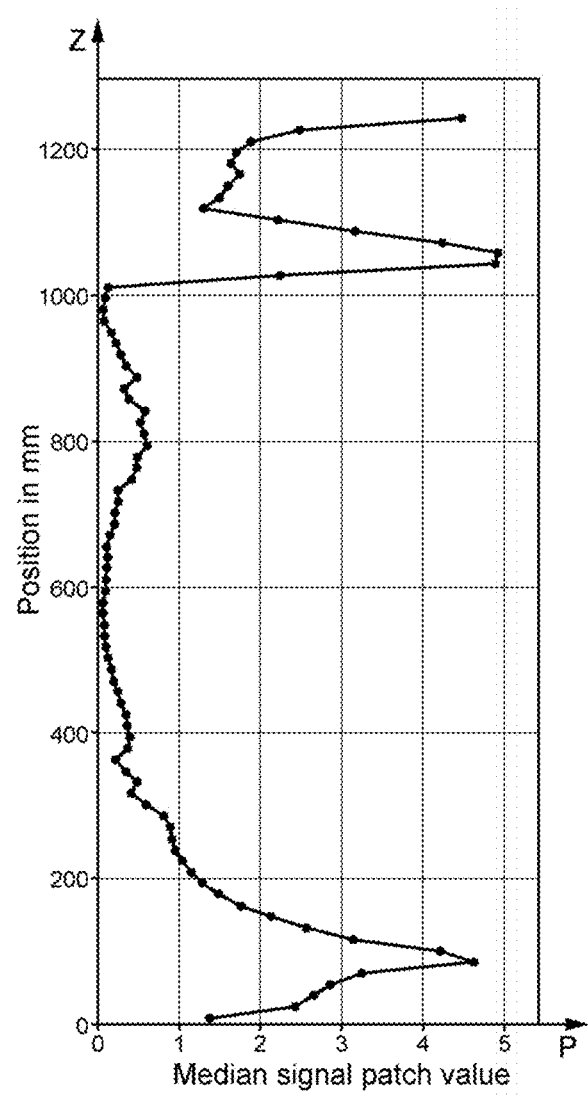
FIG. 3 shows an example of a corresponding parameter which is a median signal patch value as a function of the vertical position along the height of the patient expressed in millimeters.

FIG. 3 shows an example of a corresponding parameter P which is a median signal patch value as a function of the vertical position Z along the height of the patient expressed in millimeters. The FIG. 3 presents the corresponding fully sampled signal profile along the vertical scanning of the patient. The selected salient points are indicated in FIG. 2 on the lateral scout view by circular dots which represent the circular patch which is around 5 cm diameter.

Figure 4:
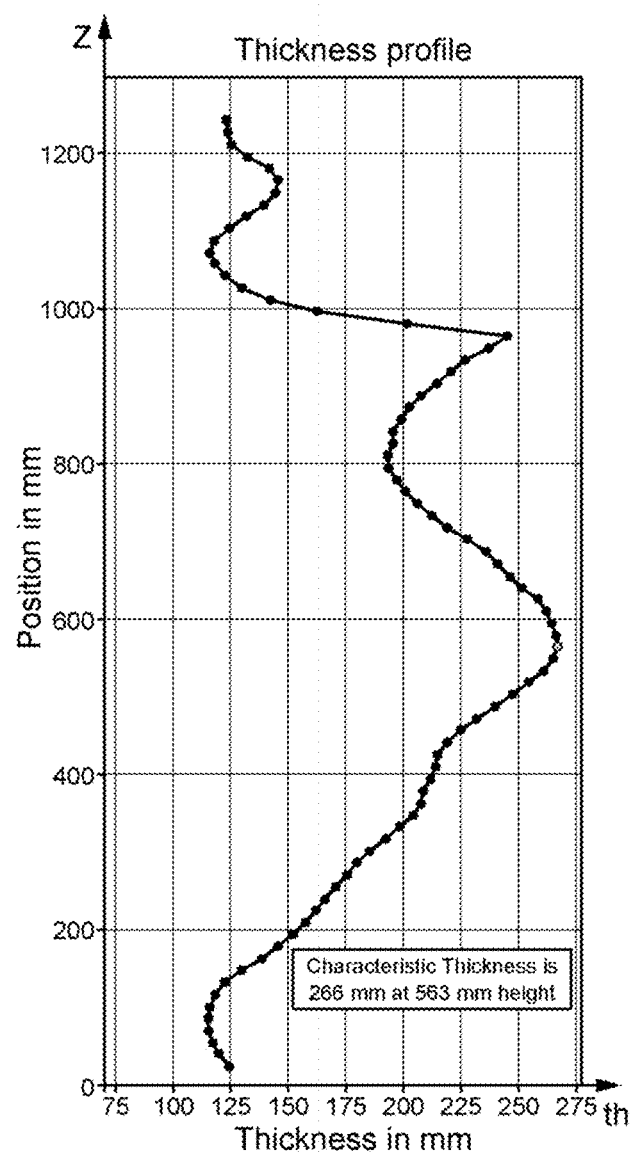
FIG. 4 shows an example of a corresponding thickness profile expressed in millimeters as a function of the vertical position along the height of the patient expressed in millimeters.

FIG. 4 shows an example of a corresponding thickness profile th expressed in millimeters as a function of the vertical position Z along the height of the patient expressed in millimeters. The FIG. 4 presents the characteristic thickness determination on the lateral profile presented in the FIG. 2.

The patient thickness profile is plotted on FIG. 4. The patient thickness th, expressed in mm, is represented as a function of the vertical position Z, also expressed in mm.

Figure 5:
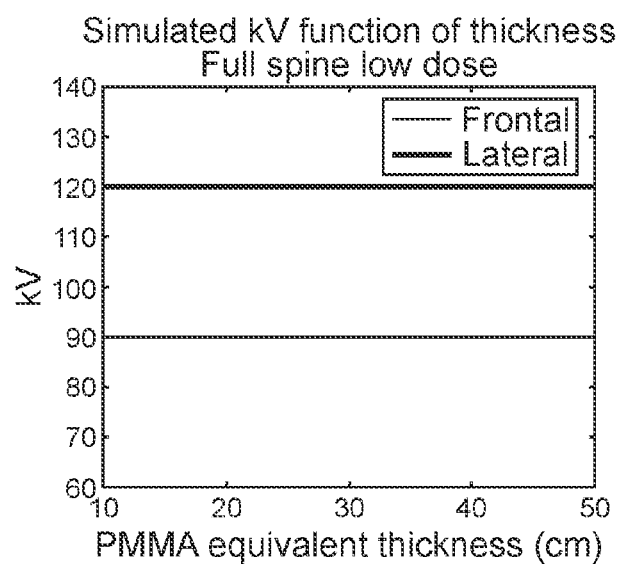
FIG. 5 shows an example of constant voltages expressed in kilovolts as a function of a patient equivalent thickness expressed in centimeters, respectively for the frontal image and for the lateral image.
Figure 6:
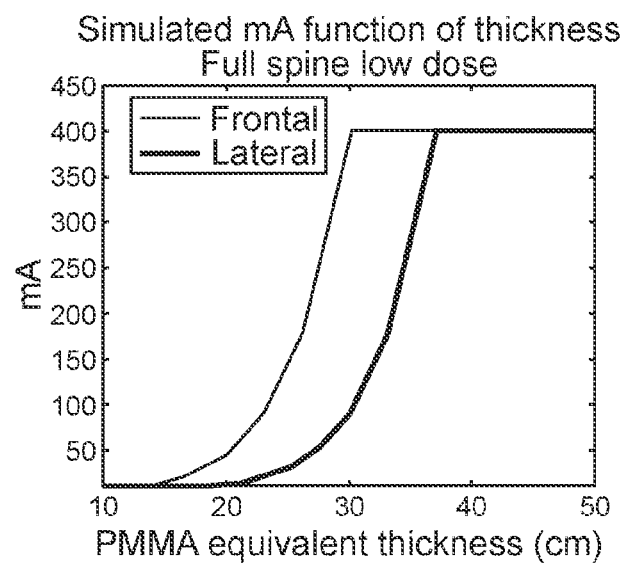
FIG. 6 shows an example of a current modulation expressed in milliamps as a function of a patient equivalent thickness expressed in centimeters, respectively for the frontal image and for the lateral image.
Figure 15:
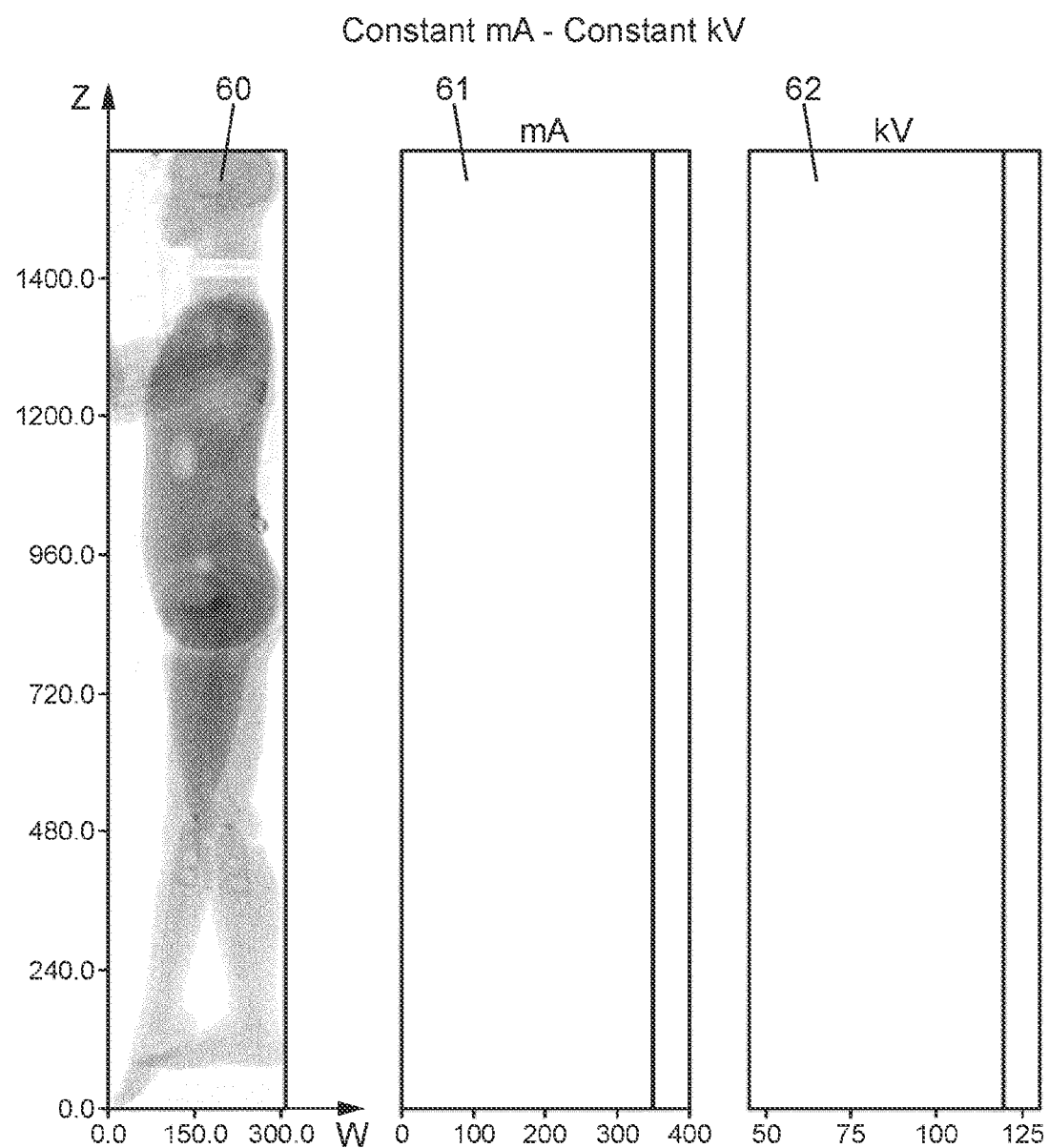
FIG. 15 shows an example of lateral image, of constant driving current intensity and of constant driving voltage intensity, in a constant current and voltage mode.
Figure 16:
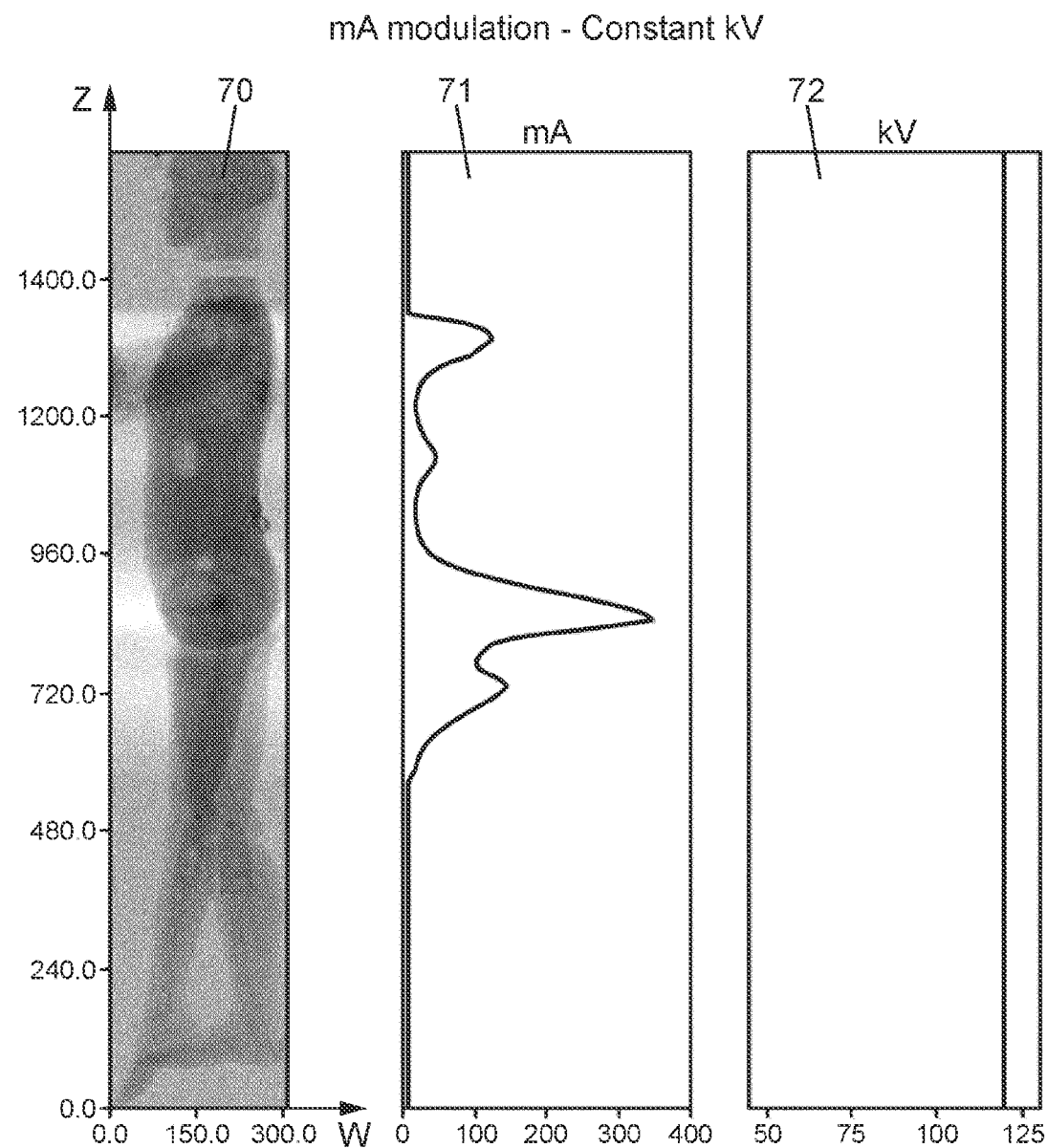
FIG. 16 shows an example of lateral image, of modulated driving current intensity and of constant driving voltage intensity, in a modulated current and constant voltage mode.
Figure 17:
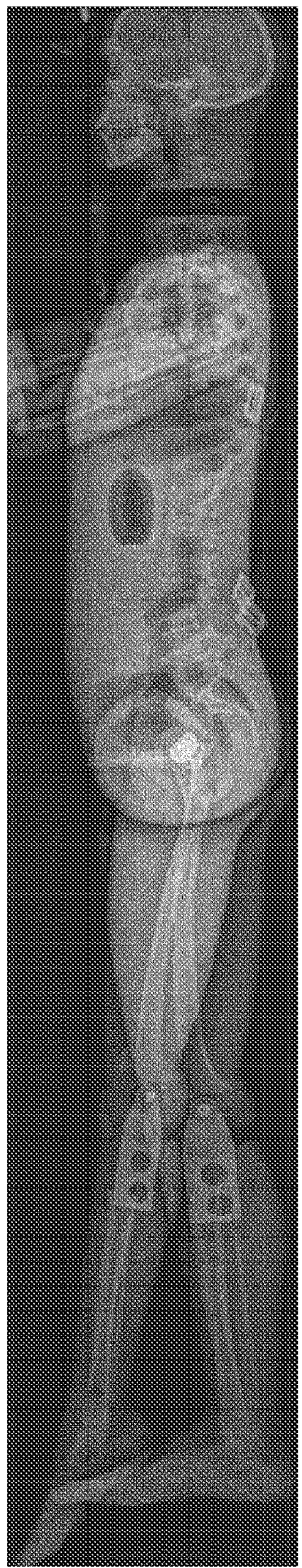
FIG. 17 shows an example of final lateral image as displayed to the radiologist.

The FIGS. 5 and 6 present a simulation of the standard relation of the voltage (kV) and current (mA) according to the equivalent PMMA thickness for the full spine protocol in "Flex Dose" mode, for the characteristic thicknesses 225 mm in frontal and 335 mm in lateral measured for the anthropomorphic phantom of the FIGS. 15, 16 and 17 taken as an example.

FIG. 5 shows an example of constant voltages V expressed in kilovolts as a function of a patient equivalent thickness th expressed in centimeters, respectively for the frontal image and for the lateral image. These constant voltages can be chosen dependent on the characteristic thicknesses measures in the frontal and lateral scout views.

For the frontal curve F, voltage constant value has been selected at 90 kV (corresponding to a characteristic thickness of 225 mm measured in the frontal scout view of the anthropomorphic phantom) and is independent on the characteristic patient thicknesses ranging from about 10 cm to about 50 cm.

For the lateral curve L, voltage constant value has been selected at 120 kV (corresponding to a characteristic thickness of 335 mm measured in the frontal scout view of the anthropomorphic phantom) and is independent on the characteristic patient thicknesses ranging from about 10 cm to about 50 cm.

FIG. 6 shows an example of a current modulation I expressed in milliamps as a function of a patient equivalent thickness th expressed in centimeters, respectively for the frontal image and for the lateral image.

For the frontal curve F, current increases regularly from about 10 mA to about 400 mA, for equivalent patient thicknesses ranging from about 10 cm to about 30 cm, and then is kept constant at about 400 mA from about 30 cm to about 50 cm.

For the lateral curve L, current increases regularly from about 10 mA to about 400 mA, for equivalent patient thicknesses ranging from about 10 cm to about 37 cm, and then is kept constant at about 400 mA from about 37 cm to about 50 cm. Increase of F curve is steeper than increase of L curve.

Figure 7:
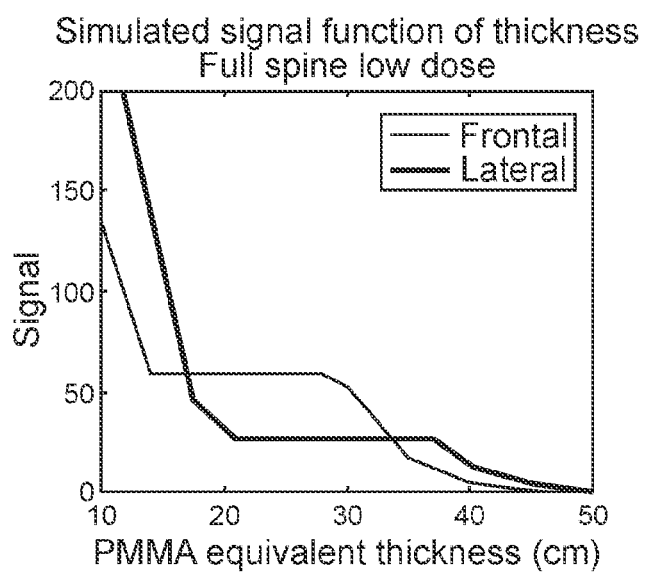
FIG. 7 shows an example of obtained numbers of X-ray photons per detector pixel (representative of signal to noise ratios) as a function of a patient equivalent thickness expressed in centimeters, respectively for the frontal image and for the lateral image.

FIG. 7 shows an example of obtained numbers S of X-ray photons per detector pixel (representative of signal to noise ratios) as a function of a patient equivalent thickness th expressed in centimeters respectively for the frontal image and for the lateral image.

For the frontal curve F, the number of X-ray photons per detector pixel is rather constant at about 60, for equivalent patient thicknesses ranging from about 15 cm to about 30 cm, and then decreases abruptly from about 60 to about 5, for equivalent patient thicknesses ranging from about 30 cm to about 40 cm, and continues to decrease more softly to tend toward zero, without reaching actually zero, from about 40 cm to about 50 cm. Below 15 cm, between 15 cm and 10 cm, this number increases abruptly to about 140.

For the lateral curve L, the number of X-ray photons per detector pixel is rather constant at about 27, for equivalent patient thicknesses ranging from about 20 cm to about 37 cm, and then decreases softly to tend toward zero, without reaching actually zero, for equivalent patient thicknesses ranging from about 40 cm to about 50 cm. Below 20 cm, between 20 cm and 10 cm, this number increases abruptly to about 250.

Figure 8:
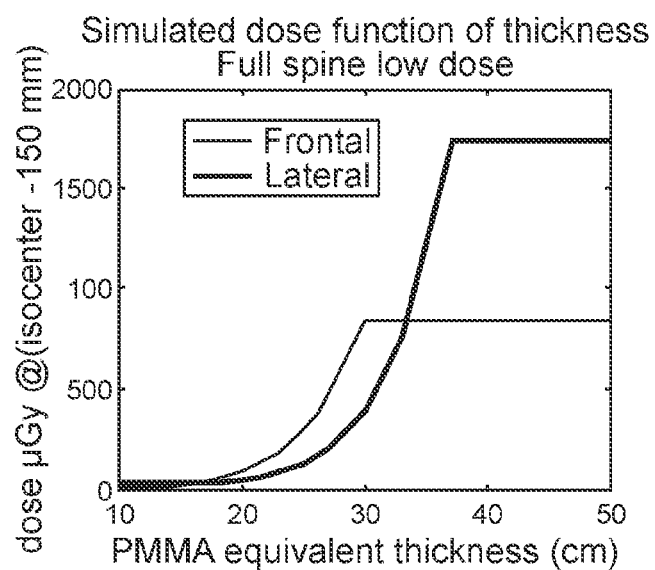
FIG. 8 shows an example of radiation dose received by patient in µGy (microgray), as a function of a patient equivalent thickness expressed in centimeters, respectively for the frontal image and for the lateral image.

FIG. 8 shows an example of radiation dose D received by patient in µGy, as a function of a patient equivalent thickness th expressed in centimeters respectively for the frontal image and for the lateral image.

For the frontal curve F, the radiation dose received by patient increases first slowly from about none to about 100 micrograys, for equivalent patient thicknesses ranging from about 10 cm to about 20 cm, then increases much more abruptly from about 100 micrograys to about 850 micrograys, for equivalent patient thicknesses ranging from about 20 cm to about 30 cm, and afterwards remains roughly constant at about 850 micrograys, for equivalent patient thicknesses ranging from about 30 cm to about 50 cm.

For the lateral curve L, the radiation dose received by patient increases first slowly from about none to about 130 micrograys, for equivalent patient thicknesses ranging from about 10 cm to about 25 cm, then increases much more abruptly from about 130 micrograys to about 1700 micrograys, for equivalent patient thicknesses ranging from about 25 cm to about 37 cm, and afterwards remains roughly constant at about 1700 micrograys, for equivalent patient thicknesses ranging from about 37 cm to about 50 cm. L curve increases more slowly than F curve in first phase of slow increase, but then L curve increases more rapidly than F curve in second phase of abrupt (or quick) increase.

On all FIGS. 9 to 16, the scale along horizontal and vertical axis are in mm, after scout view image has been binned (which means each zone of 20×20 original square pixels has been gathered in a new pixel), for scout view, frontal and lateral images taken after scout view having no such binning.

FIG. 9 to FIG. 12 show frontal and lateral images using a step of salient points detection, both before and after filtering in order to focus on the patient spine (or on the patient spine continued by one of his or her leg) and to exclude other bones, in order to enhance image contrast on the zone of interest which is here the patient spine.

This filtering step aims at selecting only salient points which are located most probably on axial skeleton, here on spine and on one leg continuing the spine.

FIG. 9 shows an example of a filtered frontal scout view, after salient points detection step, but before salient points filtering step. This patient body image is plotted with respect to altitude Z (height along vertical scanning direction) as a function of the patient width, patient thickness th being perpendicular to plan of figure, both altitude and width w being expressed in mm.

FIG. 10 shows an example of a filtered frontal scout view, after salient points detection step and after salient points filtering step. This patient body image is plotted with respect to altitude Z (height along vertical scanning direction) as a function of the patient width, patient thickness th being perpendicular to plan of figure, both altitude and width w being expressed in mm.

Bones 21 to 25 are spotted within patient 20. Patient 20 is plotted with respect to his or her height Z expressed in mm with respect to his or her width also expressed in mm.

Rules for frontal image filtering step are the following ones:

For each Z (vertical position) value, the salient point with maximal thickness is chosen, Metal parts are excluded even if they correspond to a salient point with maximal thickness (metal parts correspond to very steep attenuation or absorption changes with their vicinity within patient body).

When filtering has been performed within patient 20 frontal image:

Only remain spine 21, left leg 23 and a small part of right leg 22.

Whereas arms 24, shoulders 25 and most of right leg 22 have been filtered and thereby excluded.

FIG. 11 shows an example of a filtered lateral scout view, after salient points detection step, but before salient points filtering step. This patient body image is plotted with respect to altitude Z (height along vertical scanning direction) as a function of the patient width, patient thickness th being perpendicular to plan of figure, both altitude and width w being expressed in mm.

FIG. 12 shows an example of a filtered lateral scout view, after salient points detection step and after salient points filtering step. This patient body image is plotted with respect to altitude Z (height along vertical scanning direction) as a function of the patient width, patient thickness th being perpendicular to plan of figure, both altitude and width w being expressed in mm.

Bones 31 to 35 are spotted within patient 30. Patient 30 is plotted with respect to his or her height Z expressed in mm and with respect to his or her width also expressed in mm.

Rules for lateral image filtering step are the following ones:

For each Z (vertical position) value, the salient point closest to patient back is chosen (corresponding here to the salient point the more on the right of the lateral image since patient is looking toward left side, but it would correspond to the salient point the more on the left of the lateral image if patient were looking toward right side).

Metal parts are excluded even if they correspond to a salient point with maximal thickness (metal parts correspond to very steep attenuation or absorption changes with their vicinity within patient body), Still exclude some isolated salient points too close to the patient back, further than patient spine toward right side of lateral image, for example some isolated salient points lost in soft tissues zones like in buttocks or in flesh portion of back.

When filtering has been performed within patient 30 lateral image:

Only remain spine 31 and left leg 32,

Whereas arms 33 and 34, as well as jaws 35, have been filtered and thereby excluded.

Current intensity modulation may be calibrated.

A specific image, either frontal or lateral, may also be corrected:

A profile of driving current intensity modulation is calculated from the scout view.

Then an image is acquired with the calculated modulation profile.

Then, obtained image is corrected by calibration software homogenizing detector and correcting its non-linearity.

Then, use is made of the feedback measure file of the generator after radiation emission, in order to identify at each line j of taken image the value effectively sent by the generator of current mA (j) at this line j.

Then the image is normalized: signal of each line j of taken image is divided by mA (j).

FIG. 13 shows an example of a filtered frontal scout view, after deep neural network detection step. This patient body image is plotted with respect to altitude Z (height along vertical scanning direction) as a function of the patient width, patient thickness th being perpendicular to plan of figure, both altitude and width w being expressed in mm.

There is a patient 40 represented on a frontal image with landmarks 41 plotted by the deep neural network.

FIG. 14 shows an example of a filtered lateral scout view, after deep neural network detection step. This patient body image is plotted with respect to altitude Z (height along vertical scanning direction) as a function of the patient width, patient thickness th being perpendicular to plan of figure, both altitude and width w being expressed in mm.

There is a patient 50 represented on a lateral image with landmarks 51 plotted by the deep neural network.

FIG. 15 shows an example of lateral image, of constant driving current intensity and of constant driving voltage intensity, in a constant current and voltage mode. The FIG. 15 presents the lateral scan of an anthropomorphic phantom in the case of the modulation is disabled.

A patient 60 is represented on a lateral image. This patient body image is plotted with respect to altitude Z (height along vertical scanning direction) as a function of the patient width, patient thickness th being perpendicular to plan of figure, both altitude and width w being expressed in mm. There is a constant driving current intensity 61 all along the vertical scanning direction Z, for example at about 350 mA. There is a constant driving voltage intensity 62 all along the vertical scanning direction Z, for example at about 120 kV. Patient 60 lateral image is of average quality.

FIG. 16 shows an example of lateral image, of modulated driving current intensity and of constant driving voltage intensity, in a modulated current and constant voltage mode. The FIG. 16 presents the lateral scan of the anthropomorphic phantom in the case of the modulation is enabled but with a fixed voltage (kV).

A patient 70 is represented on a lateral image. This patient body image is plotted with respect to altitude Z (height along vertical scanning direction) as a function of the patient width, patient thickness th being perpendicular to plan of figure, both altitude and width w being expressed in mm. There is a driving current intensity modulation 71 all along the vertical scanning direction Z, for example varying between about 10 mA and about 350 mA. There is a constant driving voltage intensity 72 all along the vertical scanning direction Z, for example at about 120 kV. Patient 70 lateral image is of notably similar quality than patient 60 lateral image, but taken with a lower radiation dose and adjusted to get the right level of signal at each position along vertical scanning direction.

One can see in the image presented in the FIG. 16 compared to the one from the FIG. 15 that the blank or void part of the image outside the patient is modulated correspondingly to the modulation profile applied. The image is then corrected by the normalization with the excepted signal without attenuation to remove this modulation of the blank part in image, to avoid compromising the radiologist analysis of the image. The demodulated image follows then a standard contrast enhancement process before the presentation to the radiologist.

FIG. 17 shows an example of final lateral image as displayed to the radiologist. The FIG. 17 presents for instance the lateral scan image acquired with current modulation only including the demodulation and contrast enhancement processing as it is presented to the radiologist. This final lateral image is of good quality.

The invention has been described with reference to preferred embodiments. However, many variations are possible within the scope of the invention.

The invention claimed is:

1. A radiological imaging method comprising:
2 radiation sources with imaging directions orthogonal to each other, one frontal radiation source and one lateral radiation source, sliding vertically so as to perform vertical scanning of a standing patient along a vertical scanning direction,
wherein said radiological imaging method comprises at least one operating mode in which:
a frontal scout view is made by performing a preliminary vertical scanning of a standing patient along said vertical scanning direction by said frontal radiation source,
said frontal scout view is processed to identify a at least one specific bone localization within said frontal scout view,
a driving current intensity modulation of at least said frontal radiation source is performed along said vertical scanning direction, depending on patient thickness and on said at least one specific bone localization along said vertical scanning direction,
with no modulation of driving voltage intensity of said frontal radiation source along said vertical scanning direction,
said driving current intensity modulation of said frontal radiation source is performed automatically, so as to improve a compromise between:
lowering a global radiation dose received by the standing patient during said vertical scanning,
while keeping at a sufficient level local image contrasts of said at least one specific bone localization at different imaging positions along said vertical scanning direction, for providing a frontal image of the standing patient.

2. A radiological imaging method comprising:
2 radiation sources with imaging directions orthogonal to each other, one frontal radiation source and one lateral radiation source, sliding vertically so as to perform vertical scanning of a standing patient along a vertical scanning direction,
wherein said radiological imaging method comprises at least one operating mode in which:
a lateral scout view is made by performing a preliminary vertical scanning of a standing patient along said vertical scanning direction by said lateral radiation source,
said lateral scout view is processed to identify a at least one specific bene(s) bone localization within said lateral scout view,
a driving current intensity modulation of at least said lateral radiation source is performed along said vertical scanning direction, depending on patient thickness and on said at least one specific bone localization along said vertical scanning direction,
with no modulation of driving voltage intensity of said lateral radiation source along said vertical scanning direction,
said driving current intensity modulation of said lateral radiation source is performed automatically, so as to improve a compromise between:
lowering a global radiation dose received by the standing patient during said vertical scanning,
while keeping at a sufficient level the local image contrasts of said at least one specific bone localization at different imaging positions along said vertical scanning direction, for a lateral image of the standing patient.

3. A radiological imaging method comprising:
2 radiation sources with imaging directions orthogonal to each other, one frontal radiation source and one lateral radiation source, sliding vertically so as to perform vertical scanning of a standing patient along a vertical scanning direction,
wherein said radiological imaging method comprises at least one operating mode in which:
frontal and lateral scout views are made by performing a preliminary vertical scanning of a standing patient along said vertical scanning direction by said frontal radiation source and said lateral radiation source,
said frontal and lateral scout views are processed to identify at least one specific bone localization within both said frontal and lateral scout views,
a driving current intensity modulation of said frontal radiation source and a driving current intensity modulation of said lateral radiation source are performed along said vertical scanning direction, depending on patient thickness and on said at least one specific bone localization along said vertical scanning direction,
with no modulation of driving voltage intensities of either frontal or lateral radiation sources along said vertical scanning direction,
said driving current intensity modulation of said frontal radiation source, as well as said driving current intensity modulation of said lateral radiation source, are all performed simultaneously and automatically, so as to improve a compromise between:
lowering a global radiation received by the standing patient during said vertical scanning,
while keeping at a sufficient level local image contrasts of said at least one specific bone localization at different imaging positions along said vertical scanning direction, for a frontal image and for a lateral image of the standing patient.

4. The radiological imaging method according to claim 3, wherein at least one of said driving current intensity modulation of said frontal radiation source is performed also so as to reach a value of signal to noise ratio which is constant and common to at least a majority of said different imaging positions along said vertical scanning direction for said frontal image or said driving current intensity modulation of said lateral radiation source is performed also so as to reach a value of signal to noise ratio which is constant and common to at least a majority of said different imaging positions along said vertical scanning direction for said lateral image, and wherein said value of signal to noise ratio for said frontal image and said value of signal to noise ratio for said lateral image are the same or different.

5. The radiological imaging method according to claim 4, wherein, for each of said frontal image and said lateral image, said value of signal to noise ratio is constant and predetermined for each different organ of the standing patient to be imaged.

6. The radiological imaging method according to claim 4, wherein:
   for a frontal image of a spine of the standing patient, a standard signal to noise ratio value corresponds to a number of X-ray photons received per detector pixel comprised between 50 and 70, an operator of the radiological imaging method being able to deviate, via a manual command, from said standard signal to noise ratio value by at least + or −20%, and
   for a lateral image of a spine of the standing patient, a standard signal to noise ratio value corresponds to a number of X-ray photons received per detector pixel comprised between 20 and 40, an operator of the radiological imaging method being able to deviate, via a manual command, from said standard signal to noise ratio value by at least + or −20%.

7. The radiological imaging method according to claim 3, wherein said frontal image and/or said lateral image, after having undergone at least a first step of driving current intensity modulation, is normalized by homogenization of regions located just outside body contours of the standing patient, in order to get rid of image artifacts coming from said driving current intensity modulation.

8. The radiological imaging method according to claim 7, wherein said frontal image and/or said lateral image, after having been normalized, undergoes a contrast enhancement step.

9. The radiological imaging method according to claim 1, wherein said at least one specific bone localization excludes metallic parts of the standing patient.

10. The radiological imaging method according to claim 1, wherein said driving current intensity modulation is maximized so as to also maximize a vertical scanning speed at a constant value.

11. The radiological imaging method according to claim 1, wherein said operating mode can be either switched on or switched off manually by an operator of the radiological imaging method.

12. The radiological imaging method according to claim 3, wherein at least one of said driving current intensity modulation of said frontal radiation source or said driving current intensity modulation of said lateral radiation source is performed at a rate that does not go beyond a predetermined threshold of 5 mA per millisecond.

13. The radiological imaging method according to claim 3, wherein at least one of said driving current intensity modulation of said frontal radiation source or said driving current intensity modulation of said lateral radiation source from 20 mA to 300 mA.

14. The radiological imaging method according to claim 1, wherein said driving voltage intensity is fixed within a range from 50 kV to 120 kV.

15. The radiological imaging method according to claim 1, wherein said driving current intensity modulation is performed at a vertical scanning speed value that ranges from 8 cm/second to 20 cm/second.

16. The radiological imaging method according to claim 3, wherein each of said frontal and lateral scout views is made by performing a preliminary vertical scanning of the standing patient along a vertical scanning direction with a reduced global radiation dose as compared to each of said frontal image and said lateral image, before making each of said frontal image and said lateral image.

17. The radiological imaging method according to claim 16, wherein said reduced global radiation dose is less than 10% of said global radiation dose.

18. The radiological imaging method according to claim 1, wherein pixels in said frontal scout view are gathered together to make imaged zones.

19. The radiological imaging method according to claim 3, wherein said frontal image and said lateral image are processed to identify salient points which in turn are used to compute a thickness profile and to identify said at least one specific bone localization of the standing patient along said vertical scanning direction.

20. The radiological imaging method according to claim 3, wherein said frontal image and said lateral image are processed by a neural network to compute a thickness profile and to identify said at least one specific bone localization of the standing patient along said vertical scanning direction.

21. The radiological imaging method according to claim 1, wherein said 2 radiation sources slide vertically so as to perform vertical scanning of a pelvis or of rachis or of a spine or of an entire body of the standing patient along a vertical scanning direction.

22. The radiological imaging method according to claim 1, wherein 2 radiation detectors are respectively associated with said 2 radiation sources, said 2 radiation detectors being 2 Photon Counting Detectors (PCD) each being associated to an automatic image processing function balancing automatically image density whatever radiation dose received on a sensitive surface of said radiation detector to enhance image contrast.

23. The radiological imaging method according to claim 1, wherein 2 radiation detectors are respectively associated with said 2 radiation sources, said 2 radiation detectors being 2 multi-energy counting detectors.

* * * * *